(12) United States Patent
Marquart et al.

(10) Patent No.: US 7,906,498 B2
(45) Date of Patent: Mar. 15, 2011

(54) **CHOLESTEROL AS AN ANTIBIOTIC FOR *STREPTOCOCCUS PNEUMONIAE***

(75) Inventors: Mary E. Marquart, Jackson, MS (US); Richard J. O'Callaghan, Ridgeland, MS (US)

(73) Assignee: Board of Supervisors of Louisiana State University And Agricultural and Mechanical College, Baton Rouge, LA (US)

(*) Notice: Subject to any disclaimer, the term of this patent is extended or adjusted under 35 U.S.C. 154(b) by 785 days.

(21) Appl. No.: 11/099,854

(22) Filed: Apr. 6, 2005

(65) Prior Publication Data

US 2006/0229283 A1 Oct. 12, 2006

(51) Int. Cl.
*A61K 31/56* (2006.01)
(52) U.S. Cl. .................................. 514/178; 514/912
(58) Field of Classification Search .............. 514/178, 514/912
See application file for complete search history.

(56) References Cited

U.S. PATENT DOCUMENTS

| | | | |
|---|---|---|---|
| 4,804,539 A * | 2/1989 | Guo et al. | ...... 424/450 |
| 6,791,059 B2 | 9/2004 | Smart | |
| 6,878,899 B2 | 4/2005 | Smart | |
| 2004/0224010 A1* | 11/2004 | Hofland et al. | ...... 424/450 |

OTHER PUBLICATIONS

Baba H et al., "Essential role of domain 4 of pneumolysin from *Streptococcus pneumoniae* in cytolytic activity as determined by truncated proteins," Biochem. Biophys. Res. Commun., vol. 281, pp. 37-44 (2001).
Canvin, J.R. et al., "*Streptococcus pneumoniae* produces a second haemolysin that is distinct from pneumolysin," Microb. Pathog., vol. 22, pp. 129-132 (1997).
Ferrante, A. et al., "Inhibition of in vitro human lymphocyte response by the penumococcal toxin pneumolysin," Infect. Immun., vol. 46, pp. 585-589 (1984).
Johnson M.K. et al., "Effects of pneumolysin on human polymorphonuclear leukocytes and platelets," Infect. Immun., vol. 34, pp. 171-176 (1981).
Johnson M.K., "Properties of purified pneumococcal hemolysin." Infect. Immun. vol. 6, No. 5, pp. 755-760 (1972).
Nöllmann, M. et al., "The role of cholesterol in the activity of pneumolysin, a bacterial protein toxin," Biophysical Journal, vol. 86, pp. 3141-3151 (2002).
Reed, J.M. et al., "Ocular virulence of capsule-deficient *Streptococcus pneumoniae* in a rabbit keratitis model," IOVS, vol. 46, pp. 604-608 (2004).
Alcantara, B.B. et al., "Pneumolysin-induced complement depletion during experimental pneumococcal bacteremia," Infect. Immun., vol. 69, pp. 3569-3575 (2001).
Alexander, J.E. et al., "Amino acid changes affecting the activity of pneumolysin alter the behaviour of pneumococci in pneumonia," Microb. Pathog., vol. 24, pp. 167-174 (1998).

Baba, H. et al., "Essential role of domain 4 of pneumolysin from *Streptococcus pneumoniae* in cytolytic activity as determined by truncated proteins," Biochem. Biophys. Res. Commun., vol. 281, pp. 37-44 (2001).
Balachandran, P. et al., "The autolytic enzyme LytA of *Streptococcus pneumoniae* is not responsible for releasing pneumolysin," J. Bacteriol., vol. 183, pp. 3108-3116 (2001).
Barequet, I.S. et al., "Treatment of experimental bacterial keratitis with topical trovafloxacin," Arch. Ophthalmol., vol. 122, pp. 65-59 (2004).
Benton, K.A. et al., "Differences in virulence for mice among *Streptococcus pneumoniae* strains of capsular types 2, 3, 4, 5, and 6 are not attributable to differences in pneumolysin production," Infect. Immun., vol. 65, pp. 1237-1244 (1997).
Benton, K.A. et al., "Role of tumor necrosis factor alpha in the host response of mice to bacteremia caused by pneumolsin-deficient *Streptococcus pneumoniae*," Infect. Immun., vol. 66, pp. 839-842 (1998).
Benton, K.A. et al., "The hemolytic and complement-activating properties of pneumolysin do not contribute individually to virulence in a pneumococcal bacteremia model," Microb. Pathog., vol. 23, pp. 201-209 (1997).
Berry, A.M. et al., "Effect of defined point mutations in the pneumolysin gene on the virulence of *Streptococcus pneumoniae*," Infect. Immun., vol. 63, pp. 1969-1974 (1995).
Bharathi, M.J. et al., "In-vitro efficacy of antibacterials against bacterial isolates from corneal ulcers," Indian J. Ophthalmol., vol. 50, pp. 109-114 (2002).
Bonev, B.B. et al., "Structural analysis of the protein/lipid complexes associated with pore formation by the bacterial toxin pneumolysin," J. Biol. Chem., vol. 276, pp. 5714-5719 (2001).
Boonpasart, S. et al., "Infectious keratitis at King Chulalongkorn Memorial Hospital: a 12-year retrospective study of 391 cases," J. Med. Assoc. Thai., vol. 85, Suppl 1, pp. S217-S230 (2002).
Braun, J.S. et al., "Pneumococcal pneumolysin and $H_2O_2$ mediate brain cell apoptosis during meningitis," J. Clin. Invest., vol. 109, pp. 19-27 (2002).
Callegan, M.C. et al., "Pharmacokinetic considerations in the treatment of bacterial keratitis," Clin. Pharmacokinet., vol. 27, pp. 129-149 (1994).
Claverys, J.P. et al., "Adaptation to the environment: *Streptococcus pneumoniae*, a paradigm for recombination-mediated genetic plasticity?," Mol. Microbiol., vol. 35, pp. 251-259 (2000).
Cockeran, R. et al., "The role of pneumolysin in the pathogenesis of *Streptococcus pneumoniae* infection," Curr. Opin. Infect. Dis., vol. 15, pp. 235-239 (2002).

(Continued)

*Primary Examiner* — Zohreh A Fay
(74) *Attorney, Agent, or Firm* — Bonnie J. Davis; John H. Runnels

(57) ABSTRACT

Topical application of cholesterol has been found to be effective in preventing, treating or ameliorating the damage to the cornea caused by *Streptococcus pneumoniae*. Topical administration of cholesterol caused a significant decrease in the inflammation of the eye. In addition, cholesterol was surprisingly found to be a bactericide to *Streptococcus pneumoniae* outside the cornea. The effect of cholesterol can be enhanced by further administering a steroid or an antibiotic to the cornea.

13 Claims, 2 Drawing Sheets

OTHER PUBLICATIONS

Colino, J. et al., "Two distinct mechanisms for induction of dendritic cell apoptosis in response to intact *Streptococcus pneumoniae*," J. Immunol., vol. 171, pp. 2354-2365 (2003).

Comis, S.D. et al., "Cytotoxic effects on hair cells of guinea pig cochlea produced by pneumolysin, the thiol activated toxin of *Streptococcus pneumoniae*," Acta Otolaryngol., vol. 113, pp. 152-159 (1993).

Cutarelli, P.E. et al., "Antimicrobial activity and in vitro corneal epithelial toxicity of antimicrobial agents for gram-positive corneal pathogens," Curr. Eye Res., vol. 12, pp. 603-608 (1993).

Friedland, I.R. et al., "The limited role of pneumolysin in the pathogenesis of pneumococcal meningitis," J. Infect. Dis., vol. 172, pp. 805-809 (1995).

Gertz, R.E.J. et al., "Clonal distribution of invasive pneumococcal isolates from children and selected adults in the United States prior to 7-valent conjugate vaccine introduction," J. Clin. Microbiol., vol. 41, pp. 4194-4216 (2003).

Gritz et al., "Recurrence of microbial keratitis concomitant with antiinflammatory treatment in an animal model," Cornea, vol. 11, pp. 404-408 (1992).

Guzek, J.P. et al., "Rabbit *Streptococcus pneumoniae* keratitis model and topical therapy," Invest. Ophthalmol. Vis. Sci., vol. 39, pp. 2012-2017 (1998).

Harrison, J.C. et al., "Response of leukopenic rabbits to pneumococcal toxin," Curr. Eye Res., vol. 2, pp. 705-710 (1982).

Hoskins, J. et al., "Genome of the bacterium *Streptococcus pneumoniae* strain R6," J. Bacteriol., vol. 183, pp. 5709-5717 (2001).

Jedrzejas, M.J., "Pneumococcal virulence factors: structure and function," Microbiol. Mol. Biol. Rev., vol. 65, pp. 187-207 (2001).

Johnson, M.K. et al., "Confirmation of the role of pneumolysin in ocular infections with *Streptococcus pneumoniae*," Curr. Eye Res., vol. 11, pp. 1221-1225 (1992).

Johnson, M.K. et al., "Growth and virulence of a complement-activation-negative mutant of *Streptococcus pneumoniae* in the rabbit cornea," Curr. Eye Res., vol. 14, pp. 281-284 (1995).

Johnson, M.K. et al., "Ocular toxin of the pneumococcus," Am. J. Ophthalmol., vol. 72, pp. 175-180 (1971).

Johnson, M.K. et al., "The role of cytolysin in pneumococcal ocular infection," Am. J. Ophthalmol., vol. 80, pp. 518-521 (1995).

Johnson, M.K. et al., "The role of pneumolysin in ocular infections with *Streptococcus pneumoniae*," Curr. Eye Res., vol. 9, pp. 1107-1114 (1990).

Jounblat, R. et al., "Pneumococcal behavior and host responses during bronchopneumonia are affected differently by the cytolytic and complement-activating activities of pneumolysin," Infect. Immun., vol. 71, pp. 1813-1819 (2003).

Kadioglu, A. et al., "Upper and lower respiratory tract infection by *Streptococcus pneumoniae* is affected by pneumolysin deficiency and differences in capsule type.," Infect. Immun., vol. 70, pp. 2886-2890 (2002).

Kanclerski, K. et al., "Production and purification of *Streptococcus pneumoniae* hemolysin (pneumolysin)," J. Clin. Microbiol., vol. 25, pp. 222-225 (1987).

Kelly, S.J. et al., "Structure and molecular mechanism of a functional form of pneumolysin: a cholesterol-dependent cytolysin from *Streptococcus pneumoniae*," J. Struct. Biol., vol. 132, pp. 72-81 (2000).

Liesegang, T.J., "Bacterial Keratitis," In: Kaufman HE, Barron BA, McDonald MB (eds), The Cornea, Butterworth-Heinemann, Boston, pp. 159-218 (1998).

Magee, A.D. et al., "Requirement for capsule in colonization by *Streptococcus pneumoniae*," Infect. Immun., vol. 69, pp. 3755-3761 (2001).

Malley, R. et al., "Recognition of pneumolysin by Toll-like receptor 4 confers resistance to pneumococcal infection," Proc. Natl. Acad. Sci. U.S.A., vol. 100, pp. 1966-1971 (2003).

Mathews, M.S. et al., "*Streptococcus pneumoniae* from ophthalmic infections: serotype distribution and penicillin susceptibility," Diagn. Microbiol. Infect. Dis., vol. 36, pp. 81-84 (2000).

Parmar, P. et al., "Pneumococcal keratitis: a clinical profile," Clin. Experiment. Ophthalmol., vol. 31, pp. 44-47 (2003).

Paton, J.C. et al., "Activation of human complement by the pneumococcal toxin pneumolysin," Infect. Immun., vol. 43, pp. 1085-1087 (1984).

Paton, J.C. et al., "Molecular analysis of the pathogenicity of *Streptococcus pneumoniae*: the role of pneumococcal proteins," Annu. Rev. Microbiol., vol. 47:89-115 (1993).

Penland, R.L. et al., "Emergence of penicillin-resistant *Streptococcus pneumoniae* ocular infections," Cornea, vol. 17, pp. 135-140 (2003).

Rijneveld, A.W. et al., "Roles of interleukin-6 and macrophage inflammatory protein-2 in pneumolysin-induced lung inflammation in mice," J. Infect. Dis., vol. 185, pp. 123-126 (2002).

Rubins, J.B. et al., "Distinct roles for pneumolysin's cytotoxic and complement activities in the pathogenesis of pneumococcal pneumonia," Am. J. Respir. Crit. Care Med., vol. 153, pp. 1339-1346 (1996).

Russell, F.M. et al., "Vaccine development for capsulate bacteria causing pneumonia," Curr. Opin. Pulm. Med., vol. 9, pp. 227-232 (2003).

Schaefer, F., "Bacterial keratitis: a prospective clinical and microbiological study," Br. J. Ophthalmol., vol. 85, pp. 842-847 (2001).

Stapleton, F., "Contact lens-related microbial keratitis: what can epidemiologic studies tell us?," Eye Contact. Lens, vol. 29, pp. S85-S89 (2003).

Sutphin, J.E. et al., "Penicillin-resistant *Streptococcus pneumoniae* keratitis," Am. J. Ophthalmol., vol. 97, pp. 388-389 (1984).

Trzcinski, K. et al., "Construction of otherwise isogenic serotype 6B, 7F, 14, and 19F capsular variants of *Streptococcus pneumoniae* strain TIGR4," Appl. Environ. Microbiol., vol. 69, pp. 7364-7370 (2003).

Veenhoven, R. et al., "Effect of conjugate pneumococcal vaccine followed by polysaccharide pneumococcal vaccine on recurrent acute otitis media: a randomised study," Lancet, vol. 361, pp. 2189-2195 (2003).

Waites, K. et al., "Antimicrobial resistance among isolates of respiratory tract infection pathogens from the southern United States: data from the PROTEKT US surveillance program 2000/2001," South. Med. J., vol. 96, pp. 974-985 (2003).

Wilkins, J. et al., "Penicillin-resistant *Streptococcus pneumoniae* keratitis," Cornea, vol. 15, pp. 99-100 (1996).

Wong, T. et al., "Severe infective keratitis leading to hospital admission in New Zealand," Br. J. Ophthalmol., vol. 87, pp. 1103-1108 (2003).

\* cited by examiner

CHOLESTEROL AS AN ANTIBIOTIC FOR *STREPTOCOCCUS PNEUMONIAE*

This invention pertains to a method to prevent or ameliorate corneal damage caused by an infection due to *Streptococcus pneumoniae* by topical administration of cholesterol to the cornea.

*Streptococcus pneumoniae* ocular epidemiology. According to epidemiological studies, *Streptococcus pneumoniae* is one of the top three causes of bacterial keratitis, both in the U.S. and worldwide. See M. J. Bharathi et al., "In-vitro efficacy of antibacterials against bacterial isolates from corneal ulcers," Indian J. Ophthalmol., vol. 50, pp. 109-114 (2002); and S. Boonpasart et al., "Infectious keratitis at King Chulalongkom Memorial Hospital: a 12-year retrospective study of 391 cases," J. Med. Assoc. Thai., vol. 85, Suppl 1, pp. S217-S230 (2002). Despite the prevalence of *S. pneumoniae* as an ocular pathogen, very little attention has been given to the mechanisms and factors contributing to virulence in *S. pneumoniae* keratitis. Aside from contact lens wear, many of the risks associated with pneumococcal keratitis are typical of any type of ocular bacterial infection, including age, trauma, ocular allergy, dry eye, pre-existing viral infection, immunosuppression, or ocular surgery. See F. Stapleton, "Contact lens-related microbial keratitis: what can epidemiologic studies tell us?," Eye Contact. Lens, vol. 29, pp. S85-S89 (2003); and T. Wong et al., "Severe infective keratitis leading to hospital admission in New Zealand," Br. J. Ophthalmol., vol. 87, pp. 1103-1108 (2003). Cefazolin and benzylpenicillin (penicillin G) are routinely used to treat pneumococcal keratitis, but alternative therapies are needed due to emerging penicillin resistance. See M. S. Mathews et al., "*Streptococcus pneumoniae* from ophthalmic infections: serotype distribution and penicillin susceptibility," Diagn. Microbiol. Infect. Dis., vol. 36, pp. 81-84 (2000); J. E. Sutphin et al., "Penicillin-resistant *Streptococcus pneumoniae* keratitis," Am. J. Ophthalmol., vol. 97, pp. 388-389 (1984); and J. Wilkins et al., "Penicillin-resistant *Streptococcus pneumoniae* keratitis," Cornea, vol. 15, pp. 99-100 (1996). The complications that result from *S. pneumoniae* keratitis are loss of the eye, decreased visual acuity, or corneal perforation and scarring. See Boonpasart et al., 2002; Wong et al., 2003; P. Parmar et al., "Pneumococcal keratitis: a clinical profile," Clin. Experiment. Ophthalmol., vol. 31, pp. 44-47 (2003); and F. Schaefer, "Bacterial keratitis: a prospective clinical and microbiological study," Br. J. Ophthalmol., vol. 85, pp. 842-847 (2001). Penetrating keratoplasty must oftentimes be performed as a therapeutic measure. (Boonpasart et al., 2002).

Virulence factors. *S. pneumoniae* possesses a number of factors involved in virulence. See M. J. Jedrzejas, "Pneumococcal virulence factors: structure and function," Microbiol. Mol. Biol. Rev., vol. 65, pp. 187-207 (2001). Most of these factors are located in or on the polysaccharide capsule or cell envelope of the bacterium, with the exception of pneumolysin which formed within the cytoplasm and released to the outside of the cell. Additional factors, such as transporter proteins, choline-binding proteins, heat shock proteins, proteases and protease chaperones, and neuraminidases are also suggested to be involved in virulence, but little is known regarding their involvement in keratitis.

Capsule. *S. pneumoniae* can exist as a capsule-bearing form or as an unencapsulated form. There are at least 90 different capsular types of *S. pneumoniae*. See R. E. J. Gertz et al., "Clonal distribution of invasive pneumococcal isolates from children and selected adults in the United States prior to 7-valent conjugate vaccine introduction," J. Clin. Microbiol., vol. 41, pp. 4194-4216 (2003). The capsule is made up of polysaccharide and is the outermost physical component of the cell. The capsule aids the bacterial cell in resisting phagocytosis by polymorphonuclear leukocytes in animal models of lung infections and bacteremia, and is considered by some to be the main virulence factor of *S. pneumoniae*. See K. Trzcinski et al., "Construction of otherwise isogenic serotype 6B, 7F, 14, and 19F capsular variants of *Streptococcus pneumoniae* strain TIGR4," Appl. Environ. Microbiol., vol. 69, pp. 7364-7370 (2003). Capsule components of various strains of *S. pneumoniae* comprise the currently available 7-valent pneumonia conjugate vaccine. A major problem with this vaccine is that it does not protect against other capsular types not included in its makeup, and has been reported to be ineffective in children under 2 years of age. See F. M. Russell et al., "Vaccine development for capsulate bacteria causing pneumonia," Curr. Opin. Pulm. Med., vol. 9, pp. 227-232 (2003). Another major problem is that the genome of *S. pneumoniae* is very plastic; a cell of one capsular type can switch to another capsular type by transformation, which gives this pathogen the advantage of easily acquiring resistance to vaccination. See J. P. Claverys et al., "Adaptation to the environment: *Streptococcus pneumoniae*, a paradigm for recombination-mediated genetic plasticity?," Mol. Microbiol., vol. 35, pp. 251-259 (2000).

The literature regarding *S. pneumoniae* virulence in lung infections, bacteremia, and meningitis is composed of studies that conclude the bacterial capsule has a major role in these infections. See A. Kadioglu et al., "Upper and lower respiratory tract infection by *Streptococcus pneumoniae* is affected by pneumolysin deficiency and differences in capsule type.," Infect. Immun., vol. 70, pp. 2886-2890 (2002); and A. D. Magee et al., "Requirement for capsule in colonization by *Streptococcus pneumoniae*," Infect. Immun., vol. 69, pp. 3755-3761 (2001). Based on these conclusions, the current pneumococcal vaccine is comprised of capsule components from multiple capsular types. In addition, *S. pneumoniae* strain R6, an unencapsulated strain whose genome was recently sequenced, has long been considered to be an avirulent strain due to its lack of a capsule. See J. Hoskins et al., "Genome of the bacterium *Streptococcus pneumoniae* strain R6," J. Bacteriol., vol. 183, pp. 5709-5717 (2001). The current vaccine is reported to be ineffective in some cases. See, e.g., R. Veenhoven et al., "Effect of conjugate pneumococcal vaccine followed by polysaccharide pneumococcal vaccine on recurrent acute otitis media: a randomised study," Lancet, vol. 361, pp. 2189-2195 (2003).

Pneumolysin. Pneumolysin is a cytotoxin produced by *S. pneumoniae*. This toxin is a protein with a molecular mass of 53 kDa, and resides within the bacterial cytoplasm. See R. Cockeran et al., "The role of pneumolysin in the pathogenesis of *Streptococcus pneumoniae* infection," Curr. Opin. Infect. Dis., vol. 15, pp. 235-239 (2002); K. Kanclerski et al., "Production and purification of *Streptococcus pneumoniae* hemolysin (pneumolysin)," J. Clin. Microbiol., vol. 25, pp. 222-225 (1987); and J. C. Paton et al., "Molecular analysis of the pathogenicity of *Streptococcus pneumoniae*: the role of pneumococcal proteins," Annu. Rev. Microbiol., vol. 47:89-115 (1993). At high bacterial cell density, pneumolysin is released into the extracellular milieu. See K. A. Benton et al., "Differences in virulence for mice among *Streptococcus pneumoniae* strains of capsular types 2, 3, 4, 5, and 6 are not attributable to differences in pneumolysin production," Infect. Immun., vol. 65, pp. 1237-1244 (1997a). A cell surface protein that causes lysis of the bacteria at high cell density, autolysin, was originally thought to be responsible for releasing pneumolysin from the *S. pneumoniae* cell; however, a recent study showed that pneumolysin release was not dependent on autolysin or lysis of the cell. See P. Balachandran et al., "The autolytic enzyme LytA of *Streptococcus pneumoniae* is not responsible for releasing pneumolysin," J. Bacteriol., vol. 183, pp. 3108-3116 (2001). Due to this recent finding, the mechanism involved in pneumolysin secretion from the bacterial cell is unknown.

Pneumolysin consists of two functional domains, a pore-forming (cytolytic) domain and a complement activation domain. See R. Jounblat et al., "Pneumococcal behavior and host responses during bronchopneumonia are affected differently by the cytolytic and complement-activating activities of pneumolysin," Infect. Immun., vol. 71, pp. 1813-1819 (2003). In the case of cytolytic function, a specific structural domain of the pneumolysin molecule binds to cholesterol in the membranes of host cells and forms pores, and cholesterol is known to inhibit in vitro the cytolytic activity of pneumolysin. See M. Nöllmann et al., "The role of cholesterol in the activity of pneumolysin, a bacterial protein toxin," Biophysical Journal, vol. 86, pp. 3141-3151 (2002); H. Baba et al., "Essential role of domain 4 of pneumolysin from *Streptococcus pneumoniae* in cytolytic activity as determined by truncated proteins,", Biochem. Biophys. Res. Commun., vol. 281, pp. 37-44 (2001); B. B. Bonev et al., "Structural analysis of the protein/lipid complexes associated with pore formation by the bacterial toxin pneumolysin," J. Biol. Chem., vol. 276, pp. 5714-5719 (2001); S. J. Kelly et al., "Structure and molecular mechanism of a functional form of pneumolysin: a cholesterol-dependent cytolysin from *Streptococcus pneumoniae*," J. Struct. Biol., vol. 132, pp. 72-81 (2000); J. R. Canvin et al., "*Streptococcus pneumoniae* produces a second haemolysin that is distinct from pneumolysin," Microb. Pathog., vol. 22, pp. 129-132 (1997); and M. K. Johnson, "Properties of purified pneumococcal hemolysin," Infect. Immun., vol. 6, pp. 755-760 (1972). The binding of pneumolysin to cholesterol causes a change in the secondary structure of pneumolysin. See Kelly et al., 2000.

A separate structural domain of the pneumolysin molecule is responsible for the complement activation function, which is involved in the polymorphonuclear leukocyte migration. See M. K. Johnson et al., "Effects of pneumolysin on human polymorphonuclear leukocytes and platelets," Infect. Immun., vol. 34, pp. 171-176 (2001). The complement activation activity of pneumolysin has been reported not to be affected by the presence of cholesterol. See H. Baba et al., "Induction of gamma interferon and nitric oxide by truncated pneumoloysin that lacks pore-forming activity," Infect. Immun., vol. 70, pp. 107-113 (2002). Both cytolytic and complement-activation activities have been shown to be important for the host damage observed in pneumococcal pneumonia. Jounblat et al., 2003; and J. C. Paton et al., "Activation of human complement by the pneumococcal toxin pneumolysin," Infect. Immun., vol. 43, pp. 1085-1087 (1984).

The role of pneumolysin in disease has been found to be variable depending on the type of disease; for example, pneumolysin was found to be important for bacteremia, pneumonia, and deafness associated with meningitis, but not the inflammation associated with meningitis. See B. B. Alcantara et al., "Pneumolysin-induced complement depletion during experimental pneumococcal bacteremia," Infect. Immun., vol. 69, pp. 3569-3575 (2001); K. A. Benton et al., "Role of tumor necrosis factor alpha in the host response of mice to bacteremia caused by pneumolysin-deficient *Streptococcus pneumoniae*," Infect. Immun., vol. 66, pp. 839-842 (1998); J. E. Alexander et al., "Amino acid changes affecting the activity of pneumolysin alter the behaviour of pneumococci in pneumonia," Microb. Pathog., vol. 24, pp. 167-174 (1998); S. D. Comis et al., "Cytotoxic effects on hair cells of guinea pig cochlea produced by pneumolysin, the thiol activated toxin of *Streptococcus pneumoniae*," Acta Otolaryngol., vol. 113, pp. 152-159 (1993); and I. R. Friedland et al., "The limited role of pneumolysin in the pathogenesis of pneumococcal meningitis," J. Infect. Dis., vol. 172, pp. 805-809 (1995). In addition, the importance of the cytolytic function relative to the complement activation function of pneumolysin also varies depending on the disease. For example, the complement activation function of pneumolysin was shown to have a larger role in pneumonia in mice than the cytolytic function of pneumolysin. (Alexander et al., 1998). However, other researchers found both functions to be important, but at different times in the infection. See J. B. Rubins et al., "Distinct roles for pneumolysin's cytotoxic and complement activities in the pathogenesis of pneumococcal pneumonia," Am. J. Respir. Crit. Care Med., vol. 153, pp. 1339-1346 (1996). The complement-activating activity was demonstrated to be responsible for T cell accumulation, while the cytolytic function was responsible for neutrophil recruitment in the mouse lung. (Jounblat et al., 2003) However, in a different study, pneumolysin was shown in vitro to inhibit the immune lymphocyte proliferation response, an effect that was destroyed when pneumolysin was preincubated with cholesterol. See A. Ferrante et al., "Inhibition of in vitro human lymphocyte response by the penumococcal toxin pneumolysin," Infect. Immun., vol. 46, pp. 585-589 (1984). The cytolytic function of pneumolysin, however, was found to be more important in mouse intraperitoneal infections. See A. M. Berry et al., "Effect of defined point mutations in the pneumolysin gene on the virulence of *Streptococcus pneumoniae*," Infect. Immun., vol. 63, pp. 1969-1974 (1995). Neither the cytolytic nor the complement-activating function was individually responsible for mouse mortality in bacteremia. See K. A. Benton et al., "The hemolytic and complement-activating properties of pneumolysin do not contribute individually to virulence in a pneumococcal bacteremia model," Microb. Pathog., vol. 23, pp. 201-209 (1997b). Complement activation by pneumolysin in *S. pneumoniae* bacteremia was shown to lead to depletion of complement in complement-compromised hosts and therefore an inability to clear *S. pneumoniae* out of the blood by opsonophagocytosis. (Alcantara et al., 2001).

Pneumolysin has been found to induce apoptosis of dendritic cells, which are antigen-presenting cells important for induction of the host immune response. See J. Colino et al., "Two distinct mechanisms for induction of dendritic cell apoptosis in response to intact *Streptococcus pneumoniae*," J. Immunol., vol. 171, pp. 2354-2365 (2003). Pneumolysin also induces the release of interleukin-6 (IL-6) and tumor necrosis factor alpha (TNF-α) in macrophages, and can induce apoptosis of neuronal cells. See R. Malley et al., "Recognition of pneumolysin by Toll-like receptor 4 confers resistance to pneumococcal infection," Proc. Natl. Acad. Sci. U.S.A., vol. 100, pp. 1966-1971 (2003); and J. S. Braun et al., "Pneumococcal pneumolysin and $H_2O_2$ mediate brain cell apoptosis during meningitis," J. Clin. Invest., vol. 109, pp. 19-27 (2002). The structural domain of pneumolysin responsible for cytolytic activity has also recently been found to induce the host inflammatory response by the recruitment of polymorphonuclear leukocytes to the infection site in the lung as equally as the complement -activation domain. See A. W. Rijneveld et al., "Roles of interleukin-6 and macrophage inflammatory protein-2 in pneumolysin-induced lung inflammation in mice," J. Infect. Dis., vol. 185, pp. 123-126 (2002). These findings, in addition to those detailing the different functions of pneumolysin in different diseases, illustrate that the role of pneumolysin in *S. pneumoniae* pathogenesis is complex, tissue specific, and not well understood.

Pneumolysin in ocular pneumococcal infections. Studies aimed at elucidating ocular *S. pneumoniae* pathogenesis in animal models have been scarce. See J. M. Reed et al., "Ocular virulence of capsule-deficient *Streptococcus pneumoniae* in a rabbit keratitis model," IOVS, vol. 46, pp. 604-608 (2004). The first study of *S. pneumoniae* virulence factors in the eye was done by injecting *S. pneumoniae* cell extract into rabbit corneas and observing redness and swelling of the conjunctiva, purulent discharge from the eye, corneal opacity, and iritis. See M. K. Johnson et al., "Ocular toxin of the pneumococcus," Am. J. Ophthalmol., vol. 72, pp. 175-180 (1971). Conjunctival injection of capsular polysaccharide, however, produced no effect in the rabbit eye. It was concluded that the cell extract contained a "toxic factor" that was responsible for the damage to the eye. Pneumolysin was purified from the cell extract and injected into rabbit corneas in a subsequent study; redness and swelling of the conjunctiva as well as mucopurulent discharge ensued within three hours. See M. K. Johnson et al., "The role of cytolysin in pneumococcal ocular infection," Am. J. Ophthalmol., vol. 80, pp. 518-521 (1995). By 24 hours, the cornea was completely opaque, and opacity never completely resolved, even after 30 days. Immune-suppressed rabbits had reduced corneal opacity, discharge, and swelling following corneal injection with pneumolysin, which indicated that the immune response was important in the damage caused by *S. pneumoniae* keratitis. See J. C. Harrison et al., "Response of leukopenic rabbits to pneumococcal toxin," Curr. Eye Res., vol. 2, pp. 705-710 (1982). Furthermore, histopathological staining of the corneas of these leukopenic rabbits revealed a marked reduction in polymorphonuclear leukocytes in the corneal stroma compared to immune-competent rabbits. A strain of *S. pneumoniae* with the pneumolysin gene deleted was found to have significantly reduced virulence in the rabbit cornea than the wild type strain. See M. K. Johnson et al., "The role of pneumolysin in ocular infections with *Streptococcus pneumoniae*," Curr. Eye Res., vol. 9, pp. 1107-1114 (1990). Genetic rescue of the gene allowed for the return of full virulence. See M. K. Johnson et al., "Confirmation of the role of pneumolysin in ocular infections with *Streptococcus pneumoniae*," Curr. Eye Res., vol. 11, pp. 1221-1225 (1992). When the complement activation domain of the pneumolysin gene was deleted from *S. pneumoniae*, corneal virulence was also significantly reduced, but to a lesser extent than when the entire gene was deleted. See M. K. Johnson et al., "Growth and virulence of a complement-activation-negative mutant of *Streptococcus pneumoniae* in the rabbit cornea," Curr. Eye Res., vol. 14, pp. 281-284 (1995).

Chemotherapy of *S. pneumoniae* keratitis. Topical benzylpenicillin (penicillin G), ciprofloxacin, or cefazolin have historically been used for the treatment of *S. pneumoniae*. See Wong et al., 2003; T. J. Liesegang, "Bacterial Keratitis," In: Kaufman HE, Barron BA, McDonald MB (eds), The Cornea, Butterworth-Heinemann, Boston, pp 159-218 (1998); and M. C. Callegan et al., "Pharmacokinetic considerations in the treatment of bacterial keratitis," Clin. Pharmacokinet., vol. 27, pp. 129-149 (1994). However, resistance to antibiotics, especially penicillin, is increasing. The Centers for Disease Control and Prevention recognizes that the prevalence of drug-resistant *S. pneumoniae* (DRSP) has been increasing since the early 1990s and is a significant problem. See R. L. Penland et al., "Emergence of penicillin-resistant *Streptococcus pneumoniae* ocular infections," Cornea, vol. 17, pp. 135-140 (2003). One study of *S. pneumoniae* antibiotic resistance found 46% of the 3,867 *S. pneumoniae* clinical isolates to be penicillin-resistant. See K. Waites et al., "Antimicrobial resistance among isolates of respiratory tract infection pathogens from the southern United States: data from the PROTEKT US surveillance program 2000/2001," South. Med. J., vol. 96, pp. 974-985 (2003). Other antibiotics that have been tested with success against *S. pneumoniae* keratitis in the rabbit are the fluoroquinolones, gentamicin, and vancomycin. See I. S. Barequet et al., "Treatment of experimental bacterial keratitis with topical trovafloxacin," Arch. Ophthalmol., vol. 122, pp. 65-69 (2004); and J. P. Guzek et al., "Rabbit *Streptococcus pneumoniae* keratitis model and topical therapy," Invest. Ophthalmol. Vis. Sci., vol. 39, pp. 2012-2017 (1998). Ciprofloxacin has also been used with some success in human cases of pneumococcal keratitis. See Parmar et al., 2003. However, in vitro susceptibilities to the newer classes of fluoroquinolones by ocular isolates of *S. pneumoniae* were low. See Schaefer et al., 2001. Imipenem has been found effective against penicillin-sensitive and penicillin-resistant *S. pneumoniae* in vitro. See P. E. Cutarelli et al., "Antimicrobial activity and in vitro corneal epithelial toxicity of antimicrobial agents for gram-positive corneal pathogens," Curr. Eye Res., vol. 12, pp. 603-608 (1993).

Immune-compromised rabbits have reduced corneal disease compared to normal rabbits when challenged intrastromally with pneumolysin. Harrison et al., 1982. Steroids have been used in combination with antibiotics to treat *S. pneumoniae* and *Pseudomonas aeruginosa* keratitis in rabbits. While the use of steroids was a problem for *P. aeruginosa*-infected rabbits (causing an increase in disease recurrence after discontinuation of the antibiotics), the use of steroids was not a problem for *S. pneumoniae*-infected rabbits. See Gritz et al., "Recurrence of microbial keratitis concomitant with antiinflammatory treatment in an animal model," Cornea, vol. 11, pp. 404-408 (1992).

U.S. Patent Application No. 2004/0224010 discloses various lipid formulations for delivery of drugs to the eye.

We have found that topical application of cholesterol is effective in preventing, treating, or ameliorating damage to the cornea caused by an infection of *Streptococcus pneumoniae*. Topical administration of cholesterol caused a significant decrease in the inflammation of the eye. In addition, cholesterol was surprisingly found to be a bactericide to *Streptococcus pneumoniae* outside the cornea. The effect of cholesterol can be enhanced by further administering a steroid or an antibiotic to the cornea.

EXAMPLE 1

Materials and Methods

Figure 1:
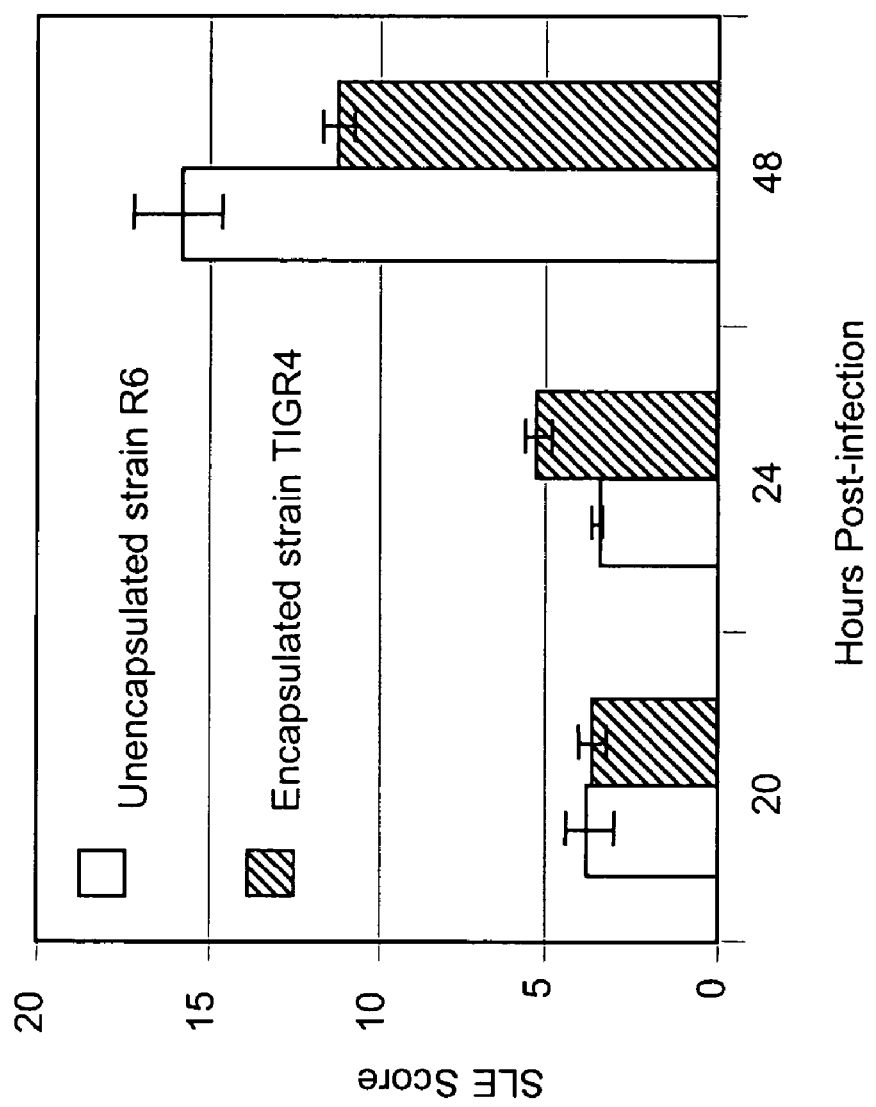
FIG. 1 illustrates the SLE scores of rabbit corneas inoculated with either an encapsulated (Avery's) strain or an unencapsulated (R6) strain of *Streptococcus pneumoniae* after 20, 24, and 48 hours post-infection.

Rabbits: New Zealand white rabbits were obtained from a commercial dealer (Myrtle's Rabbitry, Thompson Station, Tenn.). These rabbits were of both sexes and 2-3 months old. Enough rabbits were used to allow for meaningful statistics, and each experiment had two repetitions. The rabbits were housed in an animal care facility that adheres to the Federal guidelines for the care and use of laboratory animals. Rabbits were given an intramuscular injection of 50 mg/kg ketamine hydrochloride (Fort Dodge Animal Health, Fort Dodge, Iowa) and 10 mg/kg xylazine (Butler Company, Columbus, Ohio) prior to corneal injections and prior to sacrifice. Also, 0.5% proparacaine (Falcon Pharmaceuticals, Fort Worth, Tex.) was given as topical eyedrops prior to corneal injections as an added anesthesia. The method of euthanasia was an intravenous overdose of sodium pentobarbital (100 mg/kg). Unless otherwise stated, the chemicals used in the following experiments were purchased from Sigma (St. Louis, Mo.).

Innoculation of Rabbit Corneas with *S. pneumoniae*. Rabbit corneas were intrastromally inoculated with type 2 capsular and/or non-capsular *S. pneumoniae* (American Type Culture Collection, Manassas, Va.), and slit lamp examination (SLE) was used to determine the severity of keratitis at specific times following infection. *S. pneumoniae* strains were grown in Todd Hewitt broth (BD Biosciences, Sparks, Md.) to an optical density ($O.D._{600}$) of 0.3, which has been previously determined to be equivalent to $10^8$ colony-forming units per ml volume and to be mid-logarithmic growth. Cultures were diluted in medium so that each cornea received $10^5$ colony-forming units in 10 µl. Rabbits were both systemically and topically anesthetized, and their corneal stroma injected with bacteria using a tuberculin syringe. At specific times post-infection (24, 36, and 48 hours), the rabbit corneas were examined by two researchers, blind as to the identity of the strains, with a slit lamp biomicroscope (Topcon, Koakukikai K.K., Tokyo, Japan). The specific scoring system has been described by Johnson et al., 1990. The system is shown in Table 1:

TABLE 1

Scoring System for Slit Lamp Examination

| Parameter | Score | | | | |
|---|---|---|---|---|---|
| | 0 | 1 | 2 | 3 | 4 |
| Conjunctival injection | None | Trace | Mild | Moderate | Severe |
| Chemosis | None | Trace | Mild | Moderate | Severe |
| Iritis | None | Trace | Mild | Moderate | Severe |
| Fibrin | None | Trace | Mild | Moderate | Fibroid |
| Hypopyon (% of anterior chamber) | 0% | 1-25% | 26-50% | 51-75% | 76-100% |
| Stromal infiltrate (% of stroma with white cell infiltrate) | 0% | 1-25% | 26-50% | 51-75% | 76-100% |
| Stromal edema (% of stroma that is swollen) | 0% | 1-25% | 26-50% | 51-75% | 76-100% |

The two observers' scores for each parameter were averaged, and the averages of all the parameters were added for a final slit lamp examination (SLE) score. The theoretical maximum score for each cornea would be 28. A one-way analysis of variance of the Least Squares Means was used to determine if there are significant differences between capsular strains and non-capsular strains, with a P value of less than 0.05 considered significant. Six eyes were analyzed for each strain, and each experiment repeated twice.

Sacrifice of the rabbits occurred immediately following the last SLE time (48 hours post-infection) to avoid unnecessary pain. Corneas were harvested for bacterial quantification or for histopathologic analysis.

Histopathology of infected rabbit corneas. The histopathology will be conducted as described in J. J. Dajcs et al., "Corneal pathogenesis of *Staphylococcus aureus* strain Newman," Invest. Ophthalmol. Vis. Sci., vol. 43, pp. 1109-1115 (2002). Corneas will be fixed in 10% formalin immediately following removal from the rabbits, and then immersed in 10% zinc formalin overnight, dehydrated in alcohol, immersed in xylene, and embedded in paraffin. The embedded corneas will then be cut with a microtome and stained with hematoxylin and eosin. This method has been used previously to show the quantity and location of bacteria and polymorphonuclear leukocytes in rabbit corneas.

EXAMPLE 2

Role of the *S. pneumoniae* Capsule in Keratitis

Rabbit corneas were injected intrastromally with $10^5$ colony-forming units of either Avery's encapsulated strain (ATCC No. 6302, American Type Culture Collection, Manassas, Va.) (N=13) or the unencapsulated derivative strain R6 (ATCC # BAA-255)(N=11). Slit lamp examination (SLE) of the corneas using a slit lamp biomicroscope was then used to determine the severity of keratitis as described in Example 1. Two observers, blind as to the identification of the strains infecting the rabbits, assigned scores based on the severity of each of 7 parameters, and their scores were averaged. Each parameter was given a score of zero (no disease) to 4 (maximum disease), with the maximum hypothetical slit lamp score per eye as 28. The results are shown in FIG. 1.

At 24 hours post-infection, the corneal disease was mild for both the encapsulated strain and the unencapsulated strain (FIG. 1). By 48 hours post-infection, however, keratitis had progressed to a more severe state. The keratitis caused by the supposedly "avirulent" unencapsulated strain was not only apparent, but was similar to the encapsulated strain (FIG. 1, $p > 0.080$). To determine if the encapsulated strain grew well in the cornea, a determination of bacterial load was done at 20 hours post-infection. Mean bacterial log colony-forming units ±SEM recovered at 20 hours post-infection were 7.069±0.094 for the encapsulated strain and 6.533±0.116 for the non-encapsulated strain ($p=0.001$). (Data not shown) Although the number of bacterial units was statistically higher for the encapsulated stain, the non-encapsulated strain grew to a substantial number. Thus both strains were able to grow and to release toxic factors that could cause corneal damage.

EXAMPLE 3

Cholesterol as Treatment for *S. pneumoniae* Keratitis

Figure 2:
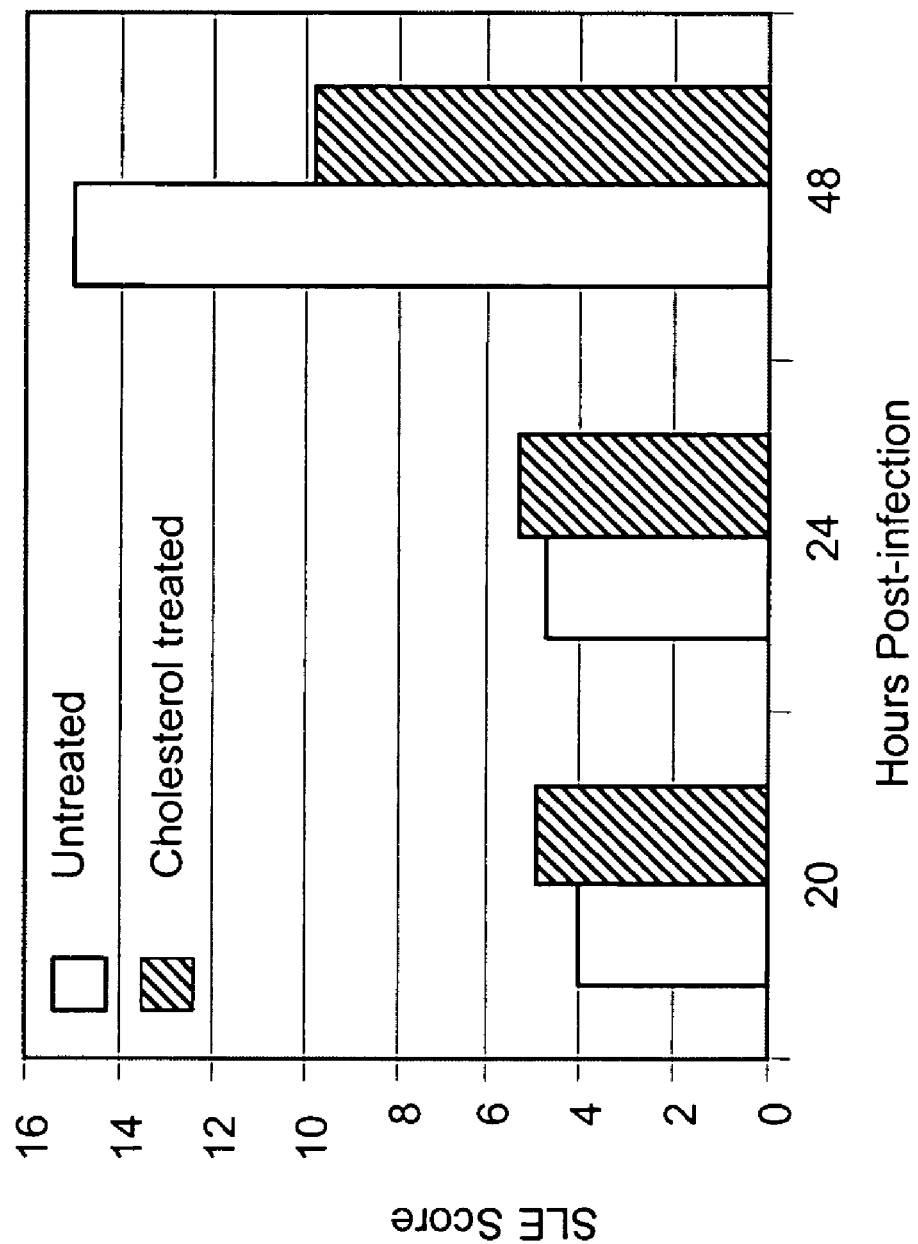
FIG. 2 illustrates the SLE scores of rabbit corneas inoculated with an encapsulated strain of *Streptococcus pneumoniae*, treated or untreated with 1% cholesterol, and examined after 20, 24, and 48 hours post-infection.

Rabbit corneas were infected with $10^5$ colony-forming units of encapsulated *S. pneumoniae*. Four rabbit corneas were treated with cholesterol while two were not treated. The cholesterol treatment consisted of topical application of 1% cholesterol in 20% glycerol at 20 and 24 hr post-infection. Control rabbits received a topical application of 20% glycerol only. Slit lamp examination (SLE) of the corneas using a slit lamp biomicroscope was then used to determine the severity of keratitis as previously described in Example 1. The results are shown in FIG. 2. Statistics were not performed due to the low sample number for the control group.

By 48 hours post-infection, the corneas treated with cholesterol were less severe than the control corneas (FIG. 2). Whereas treated and untreated corneas were essentially the same at 20 and 24 hours post-infection, the treated corneas exhibited a 35% reduction in corneal damage compare to the untreated corneas at 48 hours post-infection (FIG. 2). These observations indicated that the topical application of cholesterol ameliorated the damage associated with *S. pneumoniae* keratitis.

Bacterial loads were determined for control corneas (treated with 20% glycerol only) and corneas treated with the topical cholesterol (1% in 20% glycerol). The bacterial load in the control corneas ranged from 2.48 to 6.60 log colony-forming units, while in the treated corneas the load was 3.68 to 6.59 log colony-forming units. The similarity of the bacterial loads in the two groups demonstrates that topical application of cholesterol does not have a bactericidal effect on bacteria once inside the cornea.

To test whether 1% cholesterol might independently cause inflammation, two rabbit corneas received topical drops of 1% cholesterol in 20% glycerol over the course of 10 hours. The applications were 30 minutes apart for the first hour, and the remaining applications were 1 hour apart. The corneas were examined periodically for several days. No inflammation or adverse effect of any kind was observed following the topical treatment with cholesterol. The possible effect of cholesterol injected into the corneal stroma was also examined. One cornea received an injection of 0.5% cholesterol in 10% glycerol and a second cornea received an injection of 1% cholesterol in 20% glycerol. The corneas were examined every 2 hours for the first 8 hours, and then at 24, 30, and 48 hours post-injection. No inflammation or adverse effect was observed following injections of cholesterol.

To determine if cholesterol is bactericidal, log-phase *S. pneumoniae* were incubated with cholesterol. Three *S. pneumoniae* strains, Avery's, R6, and TIGR4, were diluted from overnight cultures and grown to log phase ($A_{600}$=0.3). These bacteria were then incubated with 1% cholesterol in 20% glycerol, 20% glycerol alone, or PBS. The optical density of each strain was determined once per hour for 3 hours, and bacterial loads were determined by plating dilutions of the bacteria onto chocolate agar. Incubation with 20% glycerol alone had no effect on bacterial growth compared to incubation with PBS, whereas incubation with 1% cholesterol in 20% glycerol caused one strain of *S. pneumoniae* (i.e, TIGR4) to die and prevented the growth of the other two strains Avery's and R6). While cholesterol prevented growth in vitro (outside the cornea), cholesterol had no effect on bacterial growth in the cornea. (See above). Topical application of cholesterol could be used to decrease the numbers of *S. pneumoniae* on the outside surface of the cornea, and inhibit bacterial infiltration of the corneal surface.

In a second experiment, rabbit corneas were infected with *Staphylococcus aureus*, which produces alpha-toxin, a major corneal virulence factor. The infected rabbit corneas were treated with cholesterol (1% in 20% glycerol) in an attempt to inhibit the damaging effects of alpha-toxin. However, the cholesterol treatment proved ineffective. (Data not shown) Purified alpha-toxin with or without cholesterol was injected into rabbit corneas as well, but again the cholesterol was ineffective at reducing the pathology associated with alpha-toxin. These results indicate that the decreased severity in keratitis by cholesterol is a specific to keratitis caused by an infection of *S. pneumoniae*.

EXAMPLE 4

Production of Pneumolysin for Analysis of Inhibition by Cholesterol In Vivo

The production and purification of pneumolysin was conducted by a modification of the method described by of K. Kanclerski et al., 1987. Briefly, *S. pneumoniae* was grown to an optical density of 1.0, and the cells were pelleted by centrifugation and lysed by sonication. A hemolysis assay using rabbit red blood cells detected the presence of pneumolysin in the cytoplasmic extract of *S. pneumoniae*, and the hemolytic titer was determined to be approximately 1:256. (Data not shown). For the hemolytic titer, the samples were serially diluted and incubated with rabbit red blood cells. Hemolysis was visualized by a uniform red color in the absence of intact cells.

The pneumolysin-containing material was applied to a column containing an anion-exchange matrix (DEAE) (Bio-Rad, Hercules, Calif.), and the pneumolysin was partially purified from this matrix as described by K. Kanclerski et al., 1987. Fractions collected from the column were assayed for hemolytic activity (Data not shown). Fractions with hemolytic activity were then serially diluted 1:2 and assayed for their hemolytic titers (Data not shown). Fractions with the highest hemolytic titers (#14-17) were pooled and concentrated.

The concentrated hemolytic material eluted from the anion-exchange matrix was then further purified by gel filtration chromatography (Sephacryl S200). Fractions collected from the column were assayed for hemolytic activity, and the hemolysis-positive fractions were then titered as described for the first round of purification. Fractions with the highest titers were assayed for purity on an SDS-polyacrylamide gel (Data not shown). The results indicated that after filtration using Sephacryl 300, the pneumolysin was pure with a molecular weight of 53 kDa.

EXAMPLE 5

Inhibition of Hemolysis by Cholesterol In Vitro

Cellular extracts and supernatants from *S. pneumoniae* at several stages of growth, beginning with early log phase and continuing through late stationary phase, will be used to test the in vitro inhibition of hemolysis by cholesterol. Both the intracellular and extracellular contents will be tested because pneumolysin resides within the bacterial cell until high cell density is attained, and at high cell density, pneumolysin is released to the extracellular milieu. Bacteria will be collected by centrifugation. The supernatants will be saved for the hemolysis assays, and the bacteria will be lysed to obtain cytoplasm containing pneumolysin. Each supernatant or extract will be incubated with rabbit red blood cells in microtiter plates, and hemolysis titers measured. Each supernatant or extract will also be incubated in the presence of different concentrations of cholesterol, and hemolysis measured. These assays will obtain the optimal concentration of cholesterol that is effective at inhibiting hemolysis at different stages of bacterial growth. Controls will include bacterial growth medium incubated with the red blood cells and the different concentrations of cholesterol plus growth medium with the red blood cells. These hemolysis assays will be conducted with both encapsulated and unencapsulated strains of *S. pneumoniae*.

EXAMPLE 6

Cholesterol Treatment of Infected Rabbit Corneas

Rabbit corneas will be inoculated with *S. pneumoniae* as described in above in Example 1. Infected corneas will be treated with topical drops of a solution of cholesterol (which is available for purchase in a soluble form) and 20% glycerol (to decrease leakage from the eye). The concentration of cholesterol used in Example 3 was 1%, which caused no adverse effects to the eyes and which will again be used. (Glycerol also caused no adverse effects to the eyes.) Other concentrations of cholesterol will also be tested to determine if they more effectively inhibit hemolysis by pneumolysin. Topical drops of the cholesterol solution will be administered for 10 hours, from 37 to 47 hours post-infection, one drop every 30 minutes for the first hour and then once per hour for the remaining 9 hours. See the schedule in Table 2.

Control rabbits will receive topical drops of 20% glycerol at the same time points as the rabbits treated with cholesterol. Corneas will be examined by two observers using slit lamp biomicroscopy as described above in Example 1; statistical analysis of the slit lamp scores will also be the same. Rabbits will be sacrificed at 48 hours post-infection. Bacterial colony-forming units will be quantified and histopathology will be performed, also as described above in Example 1. Six eyes will be analyzed for each experimental group, and each experiment will be repeated twice.

TABLE 2

Schedule for the Treatment of Infected Corneas with Cholesterol

| Experimental Group | Time Post-Infection (Hours) | | | | |
|---|---|---|---|---|---|
| | 0 | 24 | 36 | 37-38 | 38-47 | 48 |
| Control (20% glycerol) | Infect | Slit lamp | Slit lamp | 1 drop every 15 min | 1 drop every 30 min | Slit lamp, sacrifice |
| Cholesterol-treated (1% in 20% glycerol) | | | | | | |
| Other cholesterol-treated (different from 1%) | | | | | | |

EXAMPLE 7

Minimal Inhibitory Concentrations of Selected Antibiotics Against *S. pneumoniae* In Vitro Minimal inhibitory concentrations of selected antibiotics against *S. pneumoniae* will be tested using the broth dilution method as described in the guidelines of the National Committee for Clinical Laboratory Standards, "Methods for dilution antimicrobial susceptibility tests for bacteria that grow aerobically," 6th ed., Approved Standard M7-A6, Wayne, Pa. (2003). The drugs to be tested are penicillin G (a beta-lactam; Sigma), cefazolin (a beta-lactam; Sigma), ciprofloxacin (a "second generation" fluoroquinolone; Alcon Laboratories, Fort Worth, Tex.), and moxifloxacin (a "fourth generation" fluoroquinolone; Fort Worth, Tex.). This assay will allow a comparison of in vitro susceptibilities to the in vivo results obtained in the following examples.

EXAMPLE 8

Comparison of Cholesterol Treatment Alone and in Combination with Antibiotics and Steroids Rabbit corneas will be inoculated with *S. pneumoniae* as described above in Example 1. Infected corneas will be treated with topical drops of cholesterol as described above. Some corneas will also be treated with topical drops of penicillin, cefazolin, ciprofloxacin, or moxifloxacin in addition to the cholesterol. The specific concentrations of antibiotics to be used in vivo will be the same as the concentrations commonly used to treat ocular bacterial infections—10,000 U/ml penicillin G, 5% cefazolin, 0.3% ciprofloxacin, and 0.5% moxifloxacin in addition to the cholesterol. Antibiotics will be applied for 10 hours, from 37 to 47 hours post-infection, one drop every 30 minutes for the first hour and then once per hour for the remaining 9 hours. Other corneas will be treated with topical steroids in addition to the cholesterol with or without antibiotics. Steroid will be applied as modified for the treatment of *S. pneumoniae* keratitis in the rat as described in P. R. Badenoch et al., "A rat model of bacterial keratitis. Effect of antibiotics and corticosteroid," Arch. Ophthalmol., vol. 103, pp. 718-722 (1985). Prednisolone acetate (1.0%) will be applied the corneas by topical drops for 10 hours, from 37 to 47 hours post-infection, one drop every 30 minutes for the first hour and then once per hour for the remaining 9 hours. Additional groups of rabbits will be treated with each component (antibiotic or steroid) alone. Tables 3, 4, 5, and 6 summarize the treatment groups for these sets of experiments.

Corneas will be examined by two observers using slit lamp biomicroscopy as described above in Example 1, and statistical analysis of the slit lamp scores will also be the same. Rabbits will be sacrificed at 48 hours post-infection. Bacterial colony-forming units will be quantified and histopathology will be performed, also as described above in Example 1. Six eyes will be analyzed for each experimental group, and each experiment will be repeated twice.

TABLE 3

Design for the Treatment of Infected Corneas with Cholesterol, Penicillin G, and Steroid

| Group | Cholesterol (37-47 hours) | Penicillin G (37-47 hours) | Prednisolone acetate (37-47 hours) | Control (20% glycerol) 37-47 hours)* |
|---|---|---|---|---|
| 1 | ✓ | | | |
| 2 | ✓ | ✓ | | |
| 3 | ✓ | | ✓ | |
| 4 | ✓ | ✓ | ✓ | |
| 5 | | | | ✓ |
| 6 | | ✓ | | ✓ |
| 7 | | | ✓ | ✓ |
| 8 | | ✓ | ✓ | ✓ |
| 9 | ✓ | | | |

*20% glycerol is known to have no effect on infected eyes.

TABLE 4

Design for the Treatment of Infected Corneas with Cholesterol, Cefazolin, and Steroid

| Group | Cholesterol (37-47 hours) | Cefazolin (37-47 hours) | Prednisolone acetate (37-47 hours) | Control (20% glycerol) (37-47 hours)* |
|---|---|---|---|---|
| 1 | ✓ | | | |
| 2 | ✓ | ✓ | | |
| 3 | ✓ | | ✓ | |
| 4 | ✓ | ✓ | ✓ | |
| 5 | | | | ✓ |
| 6 | | ✓ | | ✓ |
| 7 | | | ✓ | ✓ |
| 8 | | ✓ | ✓ | ✓ |
| 9 | ✓ | | | |

*20% glycerol is known to have no effect on infected eyes.

TABLE 5

Design for the Treatment of Infected Corneas
with Cholesterol, Ciprofloxacin, and Steroid

| Group | Cholesterol (37-47 hours) | Ciprofloxacin (37-47 hours) | Prednisolone acetate (37-47 hours) | Control (20% glycerol) (37-47 hours)* |
|---|---|---|---|---|
| 1 | ✓ | | | |
| 2 | ✓ | ✓ | | |
| 3 | ✓ | | ✓ | |
| 4 | ✓ | ✓ | ✓ | |
| 5 | | | | ✓ |
| 6 | | ✓ | | ✓ |
| 7 | | | ✓ | ✓ |
| 8 | | ✓ | ✓ | ✓ |
| 9 | | ✓ | | |

*20% glycerol is known to have no effect on infected eyes.

TABLE 6

Design for the Treatment of Infected Corneas
with Cholesterol, Moxifloxacin, and Steroid

| Group | Cholesterol (37-47 hours) | Moxifloxacin (37-47 hours) | Prednisolone acetate (37-47 hours) | Control (20% glycerol) (37-47 hours)* |
|---|---|---|---|---|
| 1 | ✓ | | | |
| 2 | ✓ | ✓ | | |
| 3 | ✓ | | ✓ | |
| 4 | ✓ | ✓ | ✓ | |
| 5 | | | | ✓ |
| 6 | | ✓ | | ✓ |
| 7 | | | ✓ | ✓ |
| 8 | | ✓ | ✓ | ✓ |
| 9 | | ✓ | | |

*20% glycerol is already known to have no effect on infected eyes.

EXAMPLE 9

Production and Purification of Pneumolysin

Pneumolysin will be purified from *S. pneumoniae* and will subsequently be injected into rabbit corneas to test its inhibition by cholesterol in vivo. *S. pneumoniae* strain TIGR4 will be used as the source because this strain was reliable for the small-scale purification of pneumolysin as presented above in Example 4. Bacterial colonies will be isolated on chocolate agar, and will be used to inoculate Todd Hewitt broth. The volume of culture used to generate pneumolysin as described above was 1.5 L (small scale). For large scale production, the volume will be increased to 6 L or more. This subculture will be grown until $O.D._{600}=1.0$ is reached, and the bacteria will be collected by centrifugation. The bacterial cells will be suspended in the buffer to be used for anion-exchange chromatography, lysed by sonication, and the cellular debris removed by centrifugation.

The cellular extract will be subjected to three rounds of chromatography to isolate pneumolysin. The first round of chromatography will consist of anion-exchange using a DEAE resin. The second and third rounds will consist of gel filtration using Sephacryl S200 and Sephacryl S300, respectively. The assay used to identify pneumolysin-containing fractions collected from the chromatographies will be the hemolysis of rabbit red blood cells. Purity of pneumolysin, which has a molecular mass of 53 kDa, will be determined by SDS-PAGE.

EXAMPLE 10

Analysis of Cholesterol Treatment Following Corneal Injection of Purified Pneumolysin Rabbit corneas will be injected with purified pneumolysin and then treated with cholesterol to show specifically the inhibition of pneumolysin activity in vivo. Three studies will be conducted: 1) rabbit corneas will be injected with purified pneumolysin and then treated with cholesterol, 2) rabbit corneas will be pre-treated with cholesterol and then injected with purified pneumolysin and 3) rabbit corneas will be injected with a mixture of pneumolysin and cholesterol to show specifically the inhibition of pneumolysin activity in vivo. (Injection of cholesterol into the cornea, as demonstrated above, has no effect on the cornea.) For each of these three studies, 3 concentrations of pneumolysin will be used for the intrastromal injections of corneas: 0 ng (buffer alone), 50 ng, and 500 ng (Tables 7, 8, and 9). The concentration of cholesterol will be constant (1% cholesterol in 20% glycerol). Controls will include treatment with 20% glycerol (no cholesterol).

All groups will be examined by slit lamp biomicroscopy at 30 and 60 minutes post-injection, and every hour thereafter for 7 hours (and then at 10, 20, and 30 hours post-injection if needed). Rabbits from each group will be chosen at specific times post-injection for sacrifice so that histopathology of their corneas can be performed. Tables 7, 8, and 9 summarize these experiments.

TABLE 7

| Treatment of Corneas with Cholesterol following Pneumolysin Injection | | | | |
|---|---|---|---|---|
| Group | Pneumolysin Injected | Cholesterol Treatment (1% in 20% Glycerol) | Vehicle Treatment (20% Glycerol) | Slit Lamp Examination |
| 1 | None (buffer) | 0.5, 1, 2, 3, 4, 5, 6, 7, and 8 hours post-injection (and 10, 20, and 30 hours if needed) | — | At 30 minutes and 1 hour post-injection, then every hour through 8 hours and as needed* |
| 2 | None (buffer) | — | Same times as Group 1 treatment | |
| 3 | 50 ng | Same times as Group 1 treatment | — | |
| 4 | 50 ng | — | Same times as Group 1 treatment | |

TABLE 7-continued

Treatment of Corneas with Cholesterol following Pneumolysin Injection

| Group | Pneumolysin Injected | Cholesterol Treatment (1% in 20% Glycerol) | Vehicle Treatment (20% Glycerol) | Slit Lamp Examination |
|---|---|---|---|---|
| 5 | 500 ng | Same times as Group 1 treatment | — | |
| 6 | 500 ng | — | Same times as Group 1 treatment | |

TABLE 8

Pre-Treatment of Corneas with Cholesterol before Pneumolysin Injection

| Group | Pneumolysin Injected | Cholesterol Treatment (1% in 20% Glycerol) | Vehicle Treatment (20% Glycerol) | Slit Lamp Examination |
|---|---|---|---|---|
| 1 | None (buffer) | 30, 15, and 5 minutes prior to injection | — | At 30 minutes and 1 hour post-injection, then every hour through 8 hours and as needed* |
| 2 | None (buffer) | — | Same times as Group 1 treatment | |
| 3 | 50 ng | Same times as Group 1 treatment | — | |
| 4 | 50 ng | — | Same times as Group 1 treatment | |
| 5 | 500 ng | Same times as Group 1 treatment | — | |
| 6 | 500 ng | — | Same times as Group 1 treatment | |

TABLE 9

Mixing of Cholesterol with Pneumolysin before Injection of Corneas

| Group | Pneumolysin Injected | Cholesterol Treatment (1% in 20% Glycerol) | Vehicle Treatment (20% Glycerol) | Slit Lamp Examination |
|---|---|---|---|---|
| 1 | None (buffer) | Mix with buffer or pneumolysin 30 minutes prior to injection | — | At 30 minutes and 1 hour post-injection, then every hour through 8 hours and as needed* |
| 2 | None (buffer) | — | Same as Group 1 treatment | |
| 3 | 50 ng | Same as Group 1 treatment | — | |
| 4 | 50 ng | — | Same as Group 1 treatment | |
| 5 | 500 ng | Same as Group 1 treatment | — | |
| 6 | 500 ng | — | Same as Group 1 treatment | |

Topical application of cholesterol is believed to exert a protective effect against *S. pneumoniae* keratitis and also purified pneumolysin. The protection against keratitis is expected to increase with the addition of either a steroid, another anti-inflammatory drug, or an antibiotic (a bactericidal agent). Examples of steroids or other anti-inflammatory drugs include prednisolone acetate, dexamethasone sodium phosphate, and other drugs known to be effective in decreasing inflammation in the eye. Examples of antibiotics include benzylpenicillin, penicillin G, ciprofloxacin, cefazolin, gentamicin, vancomycin, ciprofloxacin, other flurorquinolones, imipenem, and other antibiotics known to be effective against *S. pneumoniae*. Histopathology is expected to show a decrease in polymorphonuclear leukocytes in the corneas of rabbits treated with cholesterol compared to those not treated with cholesterol. These results mean that cholesterol inhibits the activity of *S. pneumoniae* pneumolysin, thus decreasing ocular inflammation. Combination therapy including cholesterol as a component should be considered for keratitis patients infected with *S. pneumoniae*.

Miscellaneous

The term "therapeutically effective amount" as used herein refers to an amount of cholesterol sufficient to prevent, ameliorate or lessen the damage to a mammalian cornea caused by *S. pneumoniae* keratitis to a statistically significant degree ($p<0.05$). The term "therapeutically effective amount" therefore includes, for example, an amount sufficient to lessen the severity of the disease by a reduction of 25%, preferably by 50%, and most preferably by 90%. The dosage ranges for the administration of cholesterol are those that produce the desired effect. Generally, the dosage will vary with the stage of the keratitis. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the extent of severity of keratitis by methods well known to those in the field, and by methods taught by this specification. The preferred application is topical.

Pharmaceutically acceptable carrier preparations for administration include sterile, aqueous or non-aqueous solutions, suspensions, and emulsions. Examples of non-aqueous solvents are propylene glycol, polyethylene glycol, glycerol, vegetable oils such as olive oil, and injectable organic esters such as ethyl oleate. Aqueous carriers include water, emulsions or suspensions, including saline and buffered media. The active therapeutic ingredient may be mixed with excipients that are pharmaceutically acceptable and are compatible with the active ingredient. Suitable excipients include water, saline, dextrose, and glycerol, or combinations thereof. Preservatives and other additives may also be present such as, for example, antimicrobials, anti-oxidants, chelating agents, inert gases, and the like.

The present invention provides a method of preventing, treating, or ameliorating damage to a mammalian cornea caused by *S. pneumoniae* keratitis, comprising topically administering to a subject at risk for a disease or displaying symptoms for such disease, a therapeutically effective amount of cholesterol. It is believed that the amount of cholesterol that would be effective by topical administration is from about a 0.1% weight/volume solution to about a 10% weight/volume solution, more preferably from about 0.5% weight/volume to about 5% weight/volume, and most preferably about 1% weight/volume. To use cholesterol as a prophylactic means to decrease *S. pneumoniae* infiltration of the cornea, the cholesterol should be applied one or more times daily, more preferably twice daily.

The term "ameliorate" refers to a decrease or lessening of the symptoms or signs of the disorder being treated. The symptoms or signs that may be ameliorated include those associated with keratitis in a mammalian cornea.

The complete disclosures of all references cited in this specification are hereby incorporated by reference. In the event of an otherwise irreconcilable conflict, however, the present specification shall control.

We claim:

1. A method for inhibiting damage to a mammalian cornea infected with *Streptococcus pneumoniae*, comprising topically administering a therapeutically effective amount of soluble cholesterol in solution to a mammalian cornea that is infected with *Streptococcus pneumoniae*.

2. A method as in claim 1, additionally comprising administering a therapeutically effective amount of a steroid or an antibiotic to the cornea.

3. A method as in claim 2, wherein the steroid comprises prednisolone or dexamethasone.

4. A method as in claim 2, wherein the antibiotic comprises benzylpenicillin, penicillin G, ciprofloxacin, cefazolin, gentamicin, vancomycin, ciprofloxacin, other flurorquinolones, or imipenem.

5. A method as in claim 1, wherein the cholesterol is administered in a solution containing between about 0.1% w/v cholesterol and about 10% w/v cholesterol.

6. A method as in claim 1, wherein the cholesterol is administered in a solution containing between about 0.5% w/v cholesterol and about 5% w/v cholesterol.

7. A method as in claim 1, wherein the cholesterol is administered in a solution containing about 1% w/v cholesterol.

8. A method for inhibiting *Streptococcus pneumoniae* infiltration across the cornea of a mammalian eye, said method comprising periodically administering topically a therapeutically effective amount of soluble cholesterol in solution to a mammalian cornea that is known to have greater than average susceptibility to infiltration of *Streptococcus pneumoniae*.

9. A method as in claim 8, wherein the cholesterol is administered in a solution containing between about 0.1% w/v cholesterol and about 10% w/v cholesterol.

10. A method as in claim 8, wherein the cholesterol is administered in a solution containing between about 0.5% w/v cholesterol and about 5% w/v cholesterol.

11. A method as in claim 8, wherein the cholesterol is administered in a solution containing about 1% w/v cholesterol.

12. A method as in claim 8, wherein the cholesterol is administered one or more times daily.

13. A method as in claim 12, wherein the cholesterol is administered twice daily.

* * * * *